(12) United States Patent
Auvray et al.

(10) Patent No.: US 7,439,562 B2
(45) Date of Patent: Oct. 21, 2008

(54) PROCESS FOR MODIFYING AT LEAST ONE ELECTRICAL PROPERTY OF A NANOTUBE OR A NANOWIRE AND A TRANSISTOR INCORPORATING IT

(75) Inventors: Stéphane Auvray, Paris (FR); Jean-Philippe Bourgoin, Voisins le Bretonneux (FR); Vincent Derycke, Montigny le Bretonneux (FR); Marcelo Goffman, Palaiseau (FR)

(73) Assignee: Commissariat a l'Energie Atomique (FR)

( * ) Notice: Subject to any disclaimer, the term of this patent is extended or adjusted under 35 U.S.C. 154(b) by 273 days.

(21) Appl. No.: 10/552,855

(22) PCT Filed: Apr. 22, 2003

(86) PCT No.: PCT/EP03/08827

§ 371 (c)(1),
(2), (4) Date: Aug. 1, 2006

(87) PCT Pub. No.: WO2004/094308

PCT Pub. Date: Nov. 4, 2004

(65) Prior Publication Data

US 2007/0056063 A1 Mar. 8, 2007

(51) Int. Cl.
*C01B 31/02* (2006.01)
*G01N 27/12* (2006.01)
*H01L 51/40* (2006.01)

(52) U.S. Cl. .................. 257/253; 257/414; 257/E51.04; 438/49; 977/746; 977/847; 977/938; 977/957

(58) Field of Classification Search .................. 257/253, 257/414, E51.04; 438/49; 977/746, 847, 977/938, 957

See application file for complete search history.

(56) References Cited

U.S. PATENT DOCUMENTS

| 6,528,020 | B1 | 3/2003 | Dai et al. |
| 2001/0041160 | A1 | 11/2001 | Smalley et al. |
| 2002/0117659 | A1 | 8/2002 | Cui et al. |
| 2002/0125470 | A1 | 9/2002 | Hoenlein et al. |
| 2003/0039604 | A1 | 2/2003 | Moy et al. |

FOREIGN PATENT DOCUMENTS

EP 1 164 108 A 12/2001

OTHER PUBLICATIONS

Auvray et al., Carbon nanotube transistor optimization by chemical control of the nanotube-metal interface, Jun. 21, 2004, Appl. Phys. Lett., vol. 84, No. 25, pp. 5106-5108.*
Wilson, S.R. et al., "Advanced materials: fluorous fullerenes and nanotubes" *Tetrahedron*, Elsevier Science Publishers, vol. 58, No. 20, May 13, 2002, pp. 4041-4047.

* cited by examiner

*Primary Examiner*—Richard T. Elms
*Assistant Examiner*—Michael Lulis
(74) *Attorney, Agent, or Firm*—Alston & Bird LLP

(57) ABSTRACT

The present invention concerns a method for modyfing at least an electronic property of a carbon nanotube or nanowire comprising exposing said nanotube or nanowire to an acid having the formula (I) wherein $R_1$, $R_2$ and $R_3$ are chosen in the group comprising (H, F, Cl, Br, I) with at least one of $R_1$, $R_2$ and $R_3$ being different from H. At least part of the nanotube or nanowire may be a channel region of a field effect transistor.

25 Claims, 3 Drawing Sheets (I)

PROCESS FOR MODIFYING AT LEAST ONE ELECTRICAL PROPERTY OF A NANOTUBE OR A NANOWIRE AND A TRANSISTOR INCORPORATING IT

A single semiconducting single-wall nanotube or a nanowire e.g. a carbon nanotube (or a small group of these tubes) can be used as the channel of a field-effect transistor.

A carbon nanotube is a hollow cylinder made of carbon atoms only. These atoms are organized in an hexagonal lattice just as in a single graphite sheet. The diameter of the tube is in the 1-3 nm range while its length is from 10 nm to several tens of micrometers. This tube can be electrically conducting or semiconducting depending on the details of its atomic structure (chirality).

Among all the single-wall nanotubes, the semiconducting ones (⅔ of the tubes) can be used to manufacture field effect transistors in which they act as the channel. Such a device can be built using two main techniques (and their derivatives). These two techniques depend on the way the tube are synthesized.

The first method uses tubes manufactured by laser ablation of a graphite target (or by an arc discharge between two graphite electrodes). These tubes are used dispersed in a solvent. The transistor is made by dispersing the tubes from a solution onto a silicon wafer covered by an oxide layer (SiO2 or other dielectric material). The dispersion can be random or controlled by a self-assembly process. A portion of a nanotube is then connected to two metal electrodes used as SOURCE and DRAIN. The GATE electrode of the transistor is either underneath the tube (it can be the silicon wafer itself,) or on-top of the tube covered by a dielectric material (SiO2, HfO2, TiO2, Al2O3, ZrO2 . . . ). The second method uses tubes produce by CVD (Chemical vapor deposition) directly on the wafer. The rest of the method is similar as concerns the making of the source, drain and gate electrodes.

Such a device used in air is P-type. That means that applying a negative gate bias allows the modulation of a current composed of holes (not electrons) through the tube. Whatever the prior art method, the doping level of the tubes is not controlled during their synthesis. The tubes of the first method are usually intrinsic (undoped or lightly doped). The tubes of the second method are usually P-doped (doped with holes).

It is believed however that nanotube-based or nanowire-based transistors have an important potential for future applications in nanoelectronics, such as logic gates for processors, memories and/or sensors.

For logic gates and memory cells, a good control of the doping is important to obtain high quality performance and reproducibility. The state of the art in the field is as follows:

a) Doping

Considering a carbon nanotube connected to form a transistor, it is possible to:

dope it p-type (or n-type) in a controlled way by exposing it to NO2 (or NH3) (see J. KONG et al. "Natotube Molecular Wires as Chemical Sensors" Science n° 287, 28 Jan. 2000, pages 622-625)

dope it p-type in a non-controlled way using iodine and bromine vapors. This method has been demonstrated for "mats" (bulk material made of entangled nanotubes) but not in a transistor geometry (see R. LEE et al. Nature 388, pages 255-256 (1997) and A. M RAO et al. Nature 388, pages 257 ss (1997).

dope it n-type in a controlled way using an alkali metal (typically potassium) deposition in vacuum (see BOCKRATH et al. Physical Review B61 R10606 (2000).

dope it n-type in a "somehow" controlled way by immersing the transistor in a polymer solution (polyethylene imide) (see M. SHIM et al. Journal of American Chemical Society 123, 11512 (2001) or exposing it to butylamine or APTES vapors (see J. KONG et al. "Full and Modulated Chemical Gating of Individual Carbon Nanotubes by Organic Amin Compounds" Journal of the American Chemical Society 2890-2893 (2001).

lower the natural p-type doping in a controlled way by placing the transistor in vacuum (see COLLINS et al. Science 287, 1801 (2000): "Extreme Oxygen Sensitivity of Electronic Properties of Carbon Nanotubes".) Indeed, oxygen is partially responsible for the p-type character of the nanotube transistors. But oxygen can not be used to improve the initial p-type doping level since the initial state already corresponds to the maximum effect of oxygen.

In all these examples, the doping induces a modification of the threshold voltage and an increase of the maximum on-state current.

Nevertheless, for a given gate oxide thickness, no prior art technique is known to improve the performance of p-type transistors as concerns two important parameters: the transconductance and the subthreshold slope.

Earlier studies show that the carbon nanotube transistors are very sensitive to their environment (gas or liquid). This sensitivity can be used to make sensors. In this case, one uses the modification of the electrical characteristics of the device when it is exposed to small amounts of product to be detected. This is shown in the following references:

above-cited article "Nanotube Molecular Wires as Chemical Sensors" by J. KONG et al. pages 622-625, Science vol. 287—Jan. 2000).

Article "Toward Large Arrays of Multiplex Functionalized Carbon Nanotube Sensors for Highly Sensitive and Selective Molecular Detection" published in 2003 by P. Ql et al. (American Chemical Soc n° 10.1021).

U.S. Pat. No. 6,528,020 (DAI) "Carbon nanotube devices" granted Mar. 4, 2003.

US Patent Application "Nanosensors" 2002/0117659 (LIEBER) published Aug. 29, 2002.

A first object of the present invention is a method of modifying at least an electrical property of a carbon nanotube or nanowire which is likely to provide controlled conditions.

Another object of the present invention is a method that improves the electrical performances of a transistor incorporating it.

Another object of the invention is a method of producing a nanotube or nanowire leading to a transistor having an improved transconductance when said nanotube or nanowire is used for the channel region of said transistor.

Another object of the invention is a method leading to transistors having an improved sub-threshold slope, when said nanotube or nanowire is used as the channel region of said transistor.

Another object of the invention is a method of modifying at least an electrical property of a nanotube or nanowire, said modification being stable in air during a time frame (typically a few minutes) that is compatible with a protective step.

At least one of said objects is fulfilled by a method for modyfing at least an electronic property of a nanotube or nanowire comprising exposing said nanotube or nanowire to an acid having the formula

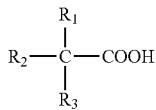

wherein $R_1$, $R_2$ and $R_3$ are chosen in the group comprising (H, F, Cl, Br, I) with at least one of $R_1$, $R_2$ and $R_3$ being different from H, which excludes acetic acid.

In a variant R1=F (monofluoroaceticacid) or R1=R2=F (difluoroaceticacid).

According to a preferred embodiment R1=R2=R3=F (trifluoro acetic acid TFA).

At least part of said nanotube or nanowire may be a channel region of a field effect transistor. It is preferable to submit the nanotube or nanowire to said exposure after the transistor is formed.

According to a variant, at least one characteristic of a transistor is measured during said exposure to an acid to monitor the exposure of the transistor (or of a group of transistor) to the acid, e.g. by using a back gate electrode.

After the exposure is completed, a dielectric layer may be brought on at least part of the nanotube or nanowire. When the final transistor uses the back-gate electrode, the protective layer may be simply the said dielectric layer. However, the final transistor may operate with at least a top gate electrode. For that purpose, at least one top gate electrode may be brought on said dielectric layer.

Preferably for a transistor used as such, said dielectric layer covers the whole surface of the nanotube or nanowire, which acts as a barrier layer to protect the nanotube or nanowire. The top gate(s) also contribute to said protection. Alternatively, in the case of a transistor used as a sensor, the dielectric layer uncovers a part (e.g. a major part) of the nanotube or nanowire, leaving in contact with the ambient atmosphere a region of the nanotube or nanowire that is suitable for its sensing function. In this case also, the protection is obtained on part of the tube or wire by an insulating layer, or by an insulating layer and a top gate electrode.

The invention also concerned a p-type nanotube or nanowire wherein an absorbed substance is

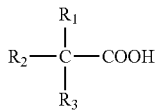

and wherein R1, R2 and R3 are chosen in the group comprising (H, F, Cl, Br, I) at least one of R1, R2 and R3 being different from H. At least part of said nanotube or nanowire may be a channel region of a field effect transistor having a source electrode, a drain electrode and at least one insulated gate electrode.

The invention will be better understood with the description hereinbelow, together with the drawings.

In the present text, the word nanotube or nanowire is meant to designate a nano-component that is capable of being used as a channel region of a field-effect transistor, or for which at least part of its length may be used as a channel region.

The method is based on preparing a nanotube or nanowire transistor according to one of the two above presented techniques and to expose it to acid vapors to modify at least one electrical property. The used acid can be one of the following: TFA trifluoro acetic acid (CF3COOH), difluoro acetic acid, monofluoro acetic acid, or the same where one or more fluor atoms are replaced by one of: chlorine, bromine or iodine. Acetic acid (without halogen atoms) does not give the required effect. The level can be adjusted precisely by controlling the exposition of the product as explained below.

The present method allows the precise control of the level of exposure with a new class of compounds (acids). This exposure leads to a significant improvement of one or more of the electrical characteristics of the transistors, in particular the transconductance and/or the subthreshold slope. The exposed nanotube or nanowire is also stable in air during a time frame that is compatible with a capping (protection) step, e.g. by $SiO_2$ deposition, or by coating with a resin.

Figure 1:
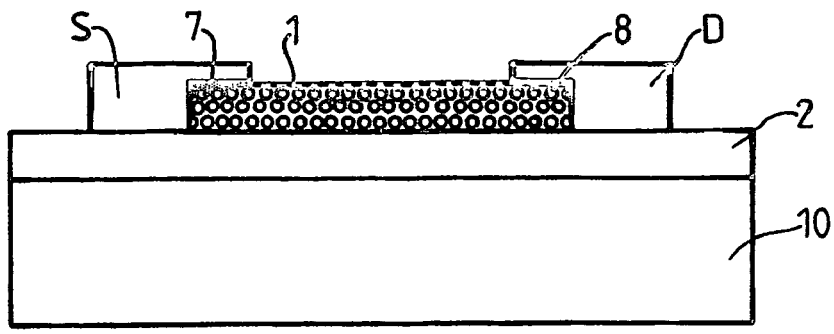
FIGS. 1 to 4 show various embodiments of a transistor comprising a nanotube or nanowire according to the present invention, FIGS. 1 to 3 being side views and FIG. 4 being a top view.

In FIG. 1, a transistor has a source electrode S and a drain electrode D connected each to a longitudinal end 7, 8 of a nanotube 1 which is supported by a dielectric layer 2 e.g. of $SiO_2$ or $Al_2O_3$. An highly doped Si substrate 10 (in the case of a $SiO_2$ back gate oxide) or an aluminium film (in the case of an $Al_2O_3$ back gate oxide) is used as a back gate electrode.

Figure 2:
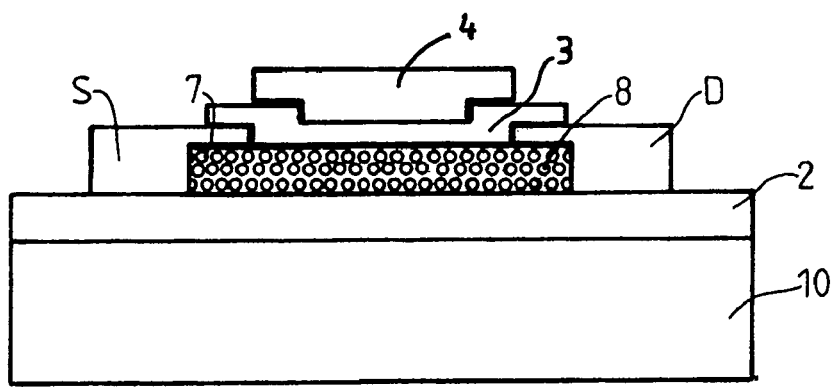

In FIG. 2, the transistor is also provided with a dielectric layer 3 e.g. made of $SiO_2$. In this embodiment, dielectric layer 3 covers all of the apparent surface of the nanotube 1 and is provided on at least a part of its surface by a top gate electrode 4.

Figure 3:
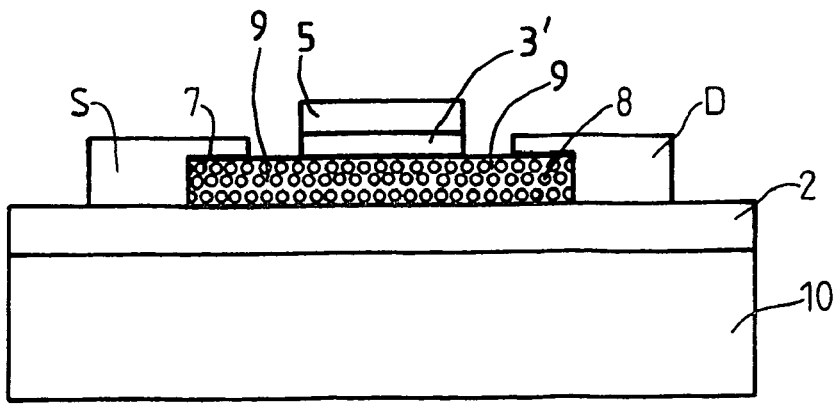

In FIG. 3, the nanotube is provided with a dielectric layer 3' covering part of its lateral surface and on which a top gate electrode 5 is deposited. In this embodiment, parts 9 of the surface of the nanotube are not covered by an insulating layer.

Figure 4:
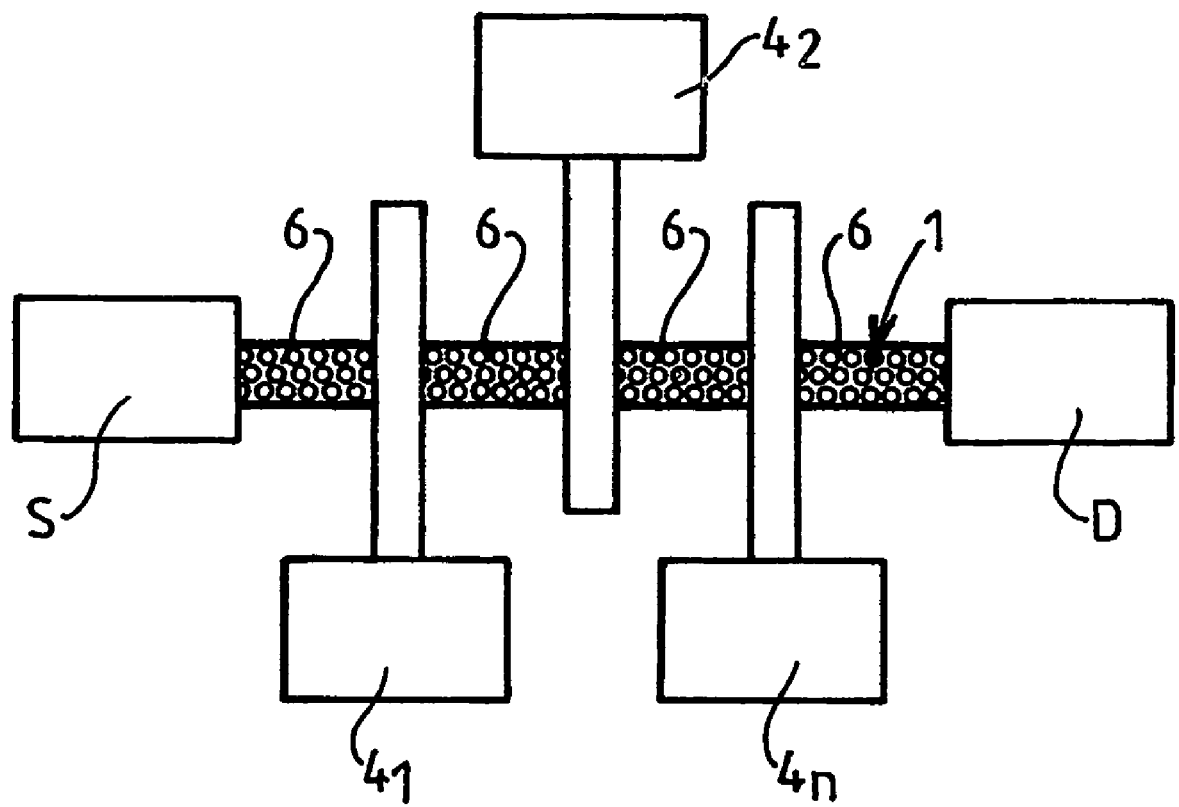

As shown in FIG. 4, there may be several gate electrodes $4_1, 4_2 \ldots 4_n$ on separated insulating regions $3_1 \ldots 3_n$, leaving uncovered regions 6 of the nanotube for example, n=5. In case the nanotube 1 is of the undoped type, these regions 6 are insulating and may be submitted to a said exposure to an acid.

Note that a multi-gate nanotube transistor is known from A. JAVEY "High-k dielectrics for advanced carbon nanotube transistors and logic gates "Nature Materials 1, 241 (2002).

In the embodiments of FIGS. 2 to 4, with one or more top gate electrodes, the step of exposing the nanotube to the acid may be done before deposition of the dielectric layer 3.

When the dielectric layer 3 covers all of the surface of the nanotube that has been exposed to said acid, the device is protected from the ambient air which protects the nanotube and contributes to the keeping of its electrical performance in the course of time.

Figure 5A:
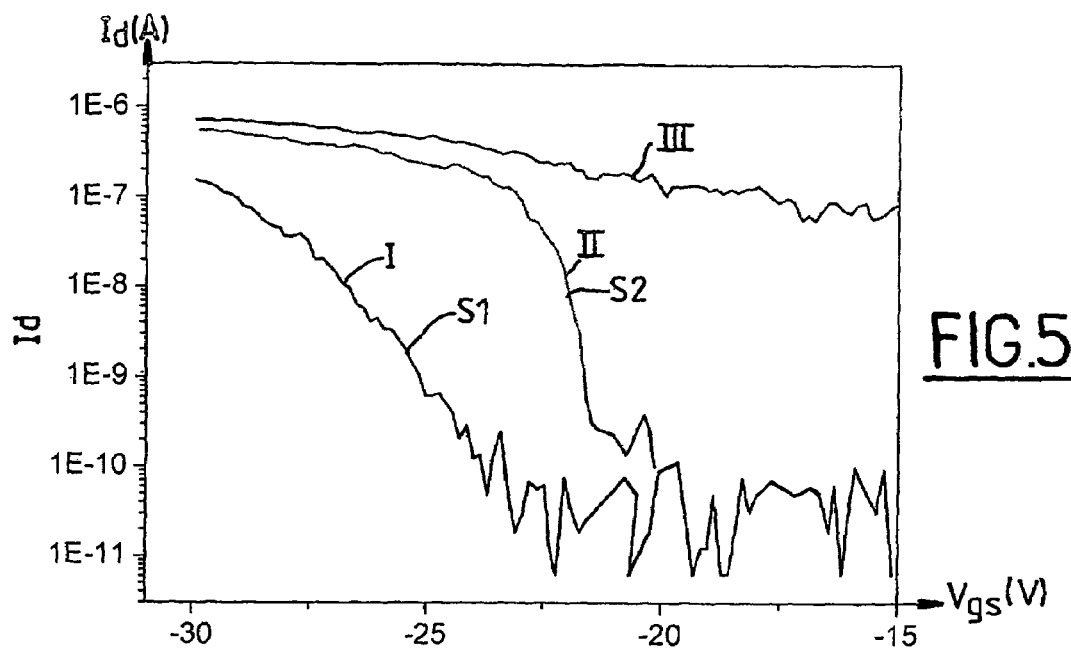
FIGS. 5a and 5b represent curves showing the modification of electrical properties of a said transistor according to the level of exposure to the prescribed acid.

FIG. 5a shows the electrical characteristic of the drain current $I_d$ as a function of the gate-source voltage Vgs (in semi-logarithmic scale), respectively before exposure trifluoro-acetic-acid (TFA) (curve I), after a first level of exposure to TFA acid (curve II) and after a second level of exposure to TFA.

Figure 5B:
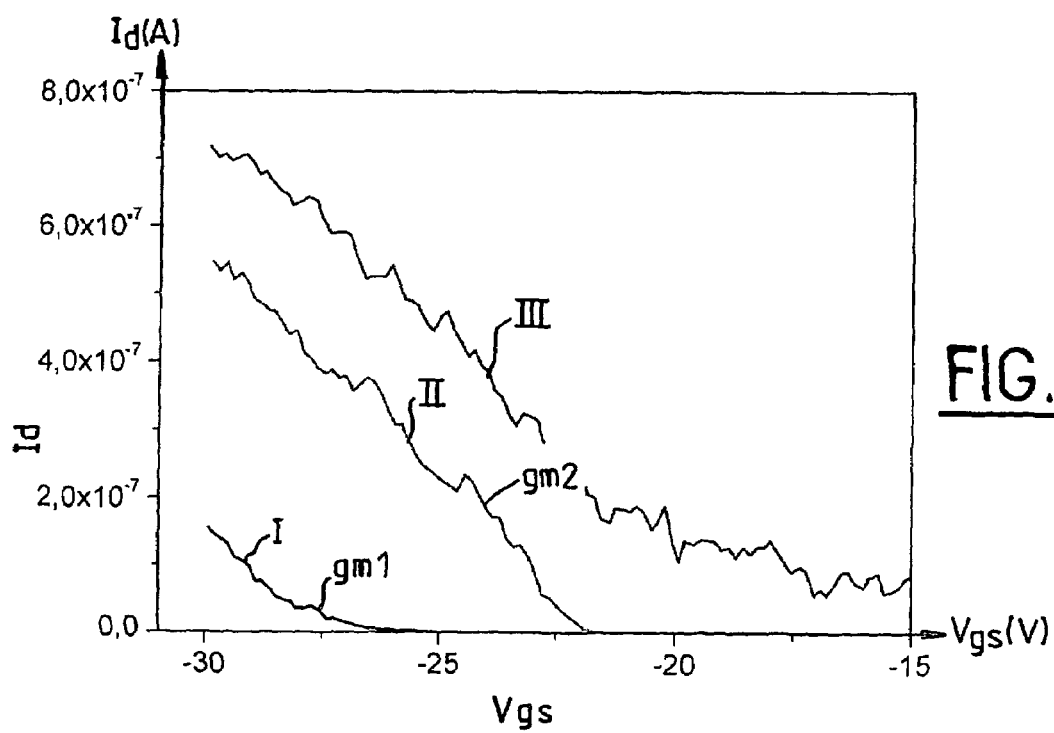

FIG. 5b shows the same curves with linear scales on both axes.

FIGS. 5a and 5b display the evolution of the electrical characteristics of the nanotube transistor before exposure to TFA vapor and after two different doses. The exposure is done in air and does not required any special equipment (vacuum chamber . . . ). The starting transistor (curve I) is "normally off" (no current flows at Vgs=0). Its threshold voltage is negative. After exposure to said acid, the current level at Vgs=0 can be so important that the device never turns off (curve III). But for an intermediate dose, the electrical characteristics can be adjusted continuously in a large range. The curve II is an example of intermediate dose. Among the parameters used to evaluate the quality of a transistor, two of the most important are the transconductance ($g_m$) and the sub-threshold slope (S). They characterize respectively in the ON- and OFF-states the response of the transistor to a modulation of the gate voltage. These two parameters are especially important for any logic or high frequency application. FIGS. 5a and 5b show clearly that the exposure to TFA vapors induces an important improvement of these two parameters, because $g_{m2}$ of curve II is significantly higher than gm1 of curve I, and $S_2$ of curve II is significantly higher than $S_1$ of curve I. With an overexposure to the acid, gm does not increase, but the sub-threshold slope is adversely affected as shows curve III of FIG. 5a.

Exposing the full length of the tube in-between the source and drain electrodes S and D induces an important performance improvement. It may be sufficient to expose selectively only one or more such sections of the tube: the sections located in the vicinity of the source and drain contacts (or, only the section close to the source contact). This is especially true when the nanotube or nanowire used has been produced by laser ablation (or arc discharge). Indeed, these tubes or wires being naturally undoped, Schottky barriers are formed at the nanotube-metal interface. These barriers limit the performance. The use of a local exposure to the prescribed acid induces the thinning and/or lowering of these barriers and thus a gain in performance.

Practically, this exposure can be realized in the geometry of FIG. 1 by using any type of protection to prevent the central part of the tube from being in contact with the acid (for example a lithography resist or a hard mask). More naturally, it can be done using the geometry of FIG. 4. In this geometry, the top gate 2 and the dielectric layer 3 cover only the central part of the tube leaving the sections close to the contacts accessible to be brought into contact with the acid.

Let us consider the case where there are several gate electrodes $4_1 \ldots 4_n$ on a single tube or wire 1 as in FIG. 4. This type of architecture does not work for naturally undoped tubes or wires because the section of the tubes that are not covered by the top-gate electrodes are insulating. To make such an architecture functional for nanotubes produced by laser ablation or arc discharge, a controlled exposure of the unprotected sections has to be made to obtain a suitable operation as a transistor.

This multi-gate architecture has been demonstrated for CVD grown nanotubes (see the above-cited article by H. JAVEY et al). These tubes are p-doped (in an uncontrolled way) during their synthesis. It has also been demonstrated for semiconductor nanowires taking advantage of the fact that these wires can be controllably doped during their growth. But this architecture can not be used for naturally undoped tubes (which are the most common tubes). In this case, a post-synthesis exposition to a said acid may be effected to obtain the requested properties to make the structure suitable as a multi-gate field effect transistor. Moreover, even if naturally doped nanotubes or nanowires are used, exposition to a said acid is likely to improve the quality of the already operational multi-gate architecture. It indeed allows in this case a fine tuning of the electrical characteristics around the starting point given by the natural doping level.

A gate on top of a section of the tube would protect the covered section from the effect of exposure. This point is however not critical because even if the entire tube gets doped (instead of the uncovered parts only), the architecture works (see the above-referenced article by H. JAVEY et al.). Still, performance should be better when the doping does not affect the covered parts because an undoped semiconductor reacts more easily to the gate electric field (lower gate bias would then be necessary).

A nanotube transistor in an open geometry (FIG. 1) is very sensitive to small doses of doping gas (especially TFA). This sensitivity can be used to make a gas sensor. In this case, modification of the electrical characteristics of the transistor are used as an indicator of the exposure level to the gas one wants to detect (in the present case TFA).

In the above description, the process has been presented as exposing the nanotube or nanowire to an acid of the defined family. The word "doping" has been purposely avoided for the following reason.

Most nanotube transistors, in particular those produced with naturally undoped tubes, operate as SCHOTTKY barrier transistors, i.e. the contact between the metal of the source S and drain D electrodes is not ohmic, and the gate voltage modulates the width of the SCHOTTKY barriers of the source and the drain. This allows or inhibits injection of carriers from the electrodes to the nanotube by tunnel effect through the barriers.

A first interpretation is that the acid is absorbed on the nanotube and accepts the electrons of the nanotube, which corresponds to the effect of a conventional p-type doping. This interpretation is supported by the fact that an operation of the transistor may be obtained where it is conductive at any gate voltage.

A second interpretation of the effect of the exposure to an acid as defined is that it improves the injection of holes. The improvement of parameter S indicates that the height of the barrier for the injection of holes is reduced after exposure to the acid. There is a correlation between such effect and the very polar nature of the molecule of acid (comprising at least an halogen atom). By absorption at the interface between the nanotube and the metal layer, the molecules of acid could favor the extraction of holes from the electrodes toward the nanotube.

A third interpretation is that the molecules of acid being absorbed both on the tube and on the electrodes, both above mentioned effects apply.

In the multi-gate embodiment of FIG. 4, where parts of the nanotube remain uncovered by the insulating layer, the only condition is that the zones that are not under the gates are not insulating. A high level of exposure (or "overexposure") as in curve III of FIGS. 5a and 5b may be successfully applied to these uncovered zones 6 of the nanotube.

The conditions for exposing the nanotube or the nanowire to the acid are not critical. The process may be performed at room temperature simply by placing the nanotube(s) on the transistor(s) above the surface of pure liquid acid.

For TFA, the vapour pressure is 140 mbar at room temperature (20° C.) which ensures that immediately above the surface of the liquid acid, the mixture of air and acid has a high concentration of acid.

The exposure may be easily monitored by continuously generating the curves of FIG. 5a and/or 5b. It is even possible to proceed to the exposure to the acid vapours until curves such as curve III are reached, and thereafter to expose the nanotube to air at ambient temperature, while still monitoring curves 5a and/or 5b to let the acid desorb.

The desorption speed between the overexposed state of curve III and an operational state as in curve II is from about a few minutes in a renewed flux of ambient air to about more than 30 minutes without appreciable renewal of the air around the nanotube. The optimal state corresponds to a transistor for which the ratio between the maximal current (in the "ON" state) and the minimal current (in the "OFF" state), the slope S and the transconductance g are maximal.

There is an appreciable range around the optimal state in which the transistor has very good or good performances so that there is no practical difficulty to determine exposure conditions for a particular type of nanotube.

The nanotube may also be exposed in a confined volume to a mixture of a neutral gas ($N_2$, Ar, ...) and of vapours of acid such as TFA. A concentration of about 1% of TFA would be a good value to ensure a sufficient exposure.

The present method although described in relation to carbon nanotubes also applies to other types of nanotubes such as boron nitride nanotubes, and also to nanowires, for examples silicium nanowires or nanowire based on a III-V compound, used as a channel region of a transistor.

States of the art transistors have nanotubes that are disposed horizontally on a surface. The present process is not limited to a specific geometry.

A way of exposing the nanotube or nanowire to an acid could also be immersion in a diluted solution of said acid.

The invention claimed is:

1. A method for modyfing at least an electronic property of a nanotube or nanowire comprising exposing said nanotube or nanowire to an acid having the formula

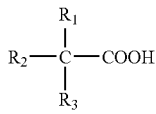

wherein $R_1$, $R_2$ and $R_3$ are chosen in the group comprising (H, F, Cl, Br, I) with at least one of $R_1$, $R_2$ and $R_3$ being different from H.

2. A method according to claim 1 wherein $R_1$=F.
3. A method according to claim 2 wherein $R_1$=$R_2$=F.
4. A method according to claim 3 wherein $R_1$=$R_2$=$R_3$=F.
5. A method according to claim 1, wherein at least part of said nanotube or nanowire is a channel region of a field effect transistor.
6. A method according to claim 5 wherein said nanotube or nanowire is submitted to said exposition after the transistor is formed.
7. A method according to claim 6 wherein at least one characteristic of the transistor is measured to monitor the modification of said at least an electronic property of the nanotube or nanowire.
8. A method according to claim 7 wherein said transistor has a back gate electrode that is used to monitor said exposure to an acid.
9. A method according to claim 8 wherein after the completion of said exposure, a dielectric layer is brought on at least part of the nanotube or nanowire.
10. A method according to claim 9 wherein at least one top gate electrode is brought on said dielectric layer.
11. A method according to claim 9 wherein said dielectric layer covers the whole surface of the nanotube or nanowire.
12. A method according to claim 6 wherein after said exposition the nanotube or nanowire is covered by an impervious layer.
13. A method as in claim 12 wherein said impervious layer is an oxide layer.
14. A method as in claim 12 wherein said impervious layer is a resin layer.
15. A method according to claim 6 wherein the transistor has several gate insulating layer regions each having a gate electrode thereon, and wherein the regions of the nanotube or nanowire between said insulated layer regions are submitted to said exposure to an acid.
16. A method as in claim 15 wherein said nanotube or nanowire is in an undoped condition before being submitted to said exposure.
17. A P-type nanotube or nanowire having an absorbed substance that is an acid having the formula:

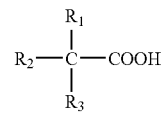

and wherein $R_1$, $R_2$ and $R_3$ are chosen in the group comprising (H, F, Cl, Br, I) at least one of $R_1$, $R_2$ and $R_3$ being different from H.

18. A nanotube or nanowire according to claim 17 wherein $R_1$=F.
19. A nanotube according claim 18 wherein $R_1$=$R_2$=F.
20. A nanotube or nanowire according to claim 19 wherein $R_1$=$R_2$=$R_3$=F.
21. A nanotube or nanowire according to claim 17, wherein at least part of said nanotube or nanowire being a channel region of a field effect transistor having a source electrode, a drain electrode and at least one insulated gate electrode.
22. A nanotube or nanowire as in claim 21 wherein said transistor is a sensor for detecting said acid.
23. A nanotube or nanowire as in claim 21 wherein at least one insulated gate electrode is disposed over the nanotube or nanowire.
24. A nanotube or nanowire as in claim 23 comprising a plurality of insulated gate electrodes disposed on undoped regions of the nanotube or nanowire and being separated by regions in which a said acid is absorbed.
25. A nanotube or nanowire as in claim 21 wherein a said insulated gate electrode is constituted by a substrate covered by an insulating region on which the nanotube or nanowire is disposed.

* * * * *